United States Patent [19]

Inoue et al.

[11] 4,053,507
[45] Oct. 11, 1977

[54] METHOD OF RECOVERING UNREACTED MATERIALS AND HEAT IN UREA SYNTHESIS

[75] Inventors: Shigeru Inoue, Kamakura; Katsumi Kagechika, Yokohama, both of Japan

[73] Assignee: Mitsui Toatsu Chemicals, Incorporated, Tokyo, Japan

[21] Appl. No.: 746,893

[22] Filed: Dec. 2, 1976

[30] Foreign Application Priority Data

Dec. 5, 1975  Japan .................................. 50-143858

[51] Int. Cl.² ........................................... C07C 126/02
[52] U.S. Cl. ................................................ 260/555 A
[58] Field of Search .................................... 260/555 A

[56] References Cited

U.S. PATENT DOCUMENTS

| 3,232,983 | 1/1966 | Flinn ................... | 260/555 A |
|---|---|---|---|
| 3,506,710 | 4/1970 | Inoue et al. ........... | 260/555 A |
| 3,573,173 | 3/1971 | Otsuka et al. ......... | 260/555 A |
| 3,636,106 | 1/1972 | Villiers-Fisher et al. | 260/555 A |
| 3,725,210 | 4/1973 | Otsuka et al. ......... | 260/555 A |
| 3,944,605 | 3/1976 | Inoue et al. ........... | 260/555 A |
| 4,003,801 | 1/1977 | Chikaoka et al. ...... | 260/555 A X |

FOREIGN PATENT DOCUMENTS

| 45-15015 | 1/1967 | Japan ........................... | 260/555 A |

Primary Examiner—Edward J. Meros
Attorney, Agent, or Firm—Arnold B. Christen; Eugene Sabol

[57] ABSTRACT

Urea synthesis effluent obtained by reacting carbon dioxide with ammonia is subjected to a plurality of decomposition stages, e.g., three stages, to decompose and recover the unreacted ammonium carbamate with stepwise reduction of pressure, and the off-gas is absorbed in an absorbent in each stage and is recovered. The aqueous urea solution from the final decomposition stage is concentrated, water vapor generated upon said concentration is condensed, and the condensate containing small amounts of ammonia and carbon dioxide is stripped with steam recovered from the high pressure absorption zone. The steam discharged from the stripping step is introduced into the final decomposition stage to directly heat the urea synthesis effluent.

14 Claims, 1 Drawing Figure

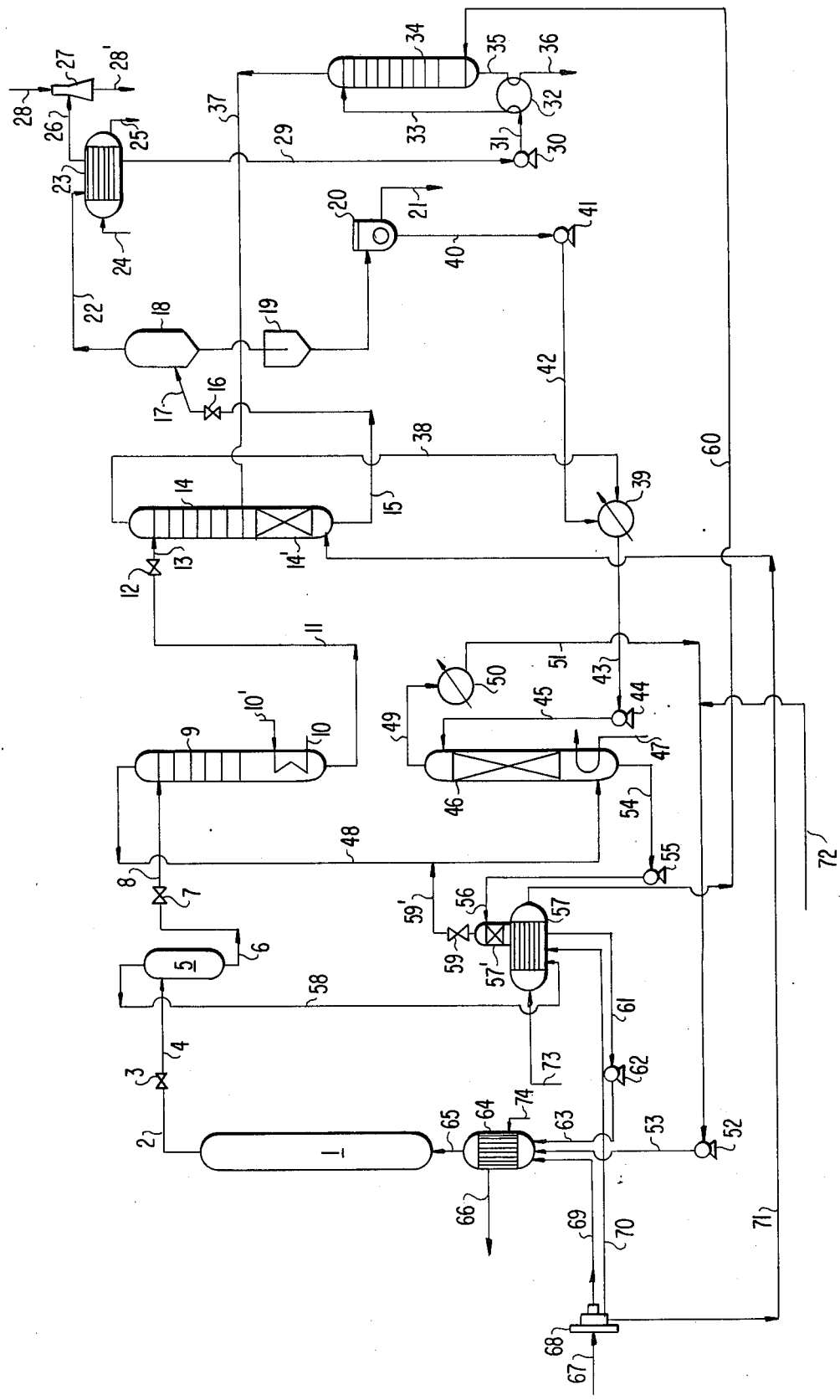

METHOD OF RECOVERING UNREACTED MATERIALS AND HEAT IN UREA SYNTHESIS

BACKGROUND OF THE INVENTION

1. Field of the Invention

The present invention relates to a process for recovering unreacted ammonia and carbon dioxde from a urea synthesis effluent obtained by reacting carbon dioxide and ammonia and, more particularly, to a process for effectively recovering heat and for recovering ammonia, by use of the recovered heat, from condensed water which is obtained by condensing water vapor evaporated upon concentration of an aqueous urea solution.

2. Description of the Prior Art

In the production of urea by the so-called total solution recycle process, starting ammonia and carbon dioxide are reacted with each other under high temperature and high pressure conditions conventionally known and recognized by those skilled in the art as urea synthesis conditions to obtain a urea synthesis effluent. The urea synthesis effluent containing unreacted ammonia and ammonium carbamate is generally subjected to a plurality of decomposition stages by stripping or distillation using stepwise reduced pressure to decompose the unreacted materials and to separate them from the urea synthesis effluent at each stage as an off-gas consisting of a mixed gas of ammonia, carbon dioxide and water vapor. The off-gases separated in the respective stages are each absorbed in an absorbent, which is fed from the absorption zone corresponding with the stripping or distillation zone of the next lower decomposition stage, under substantially the same pressure as the pressure in each of the stages where the off-gas has been separated. The resulting absorbates are used as absorbents in the respective higher pressure stages. The off-gases separated in the respective stages are thus absorbed by turn and the final absorbate discharged from the absorption zone of the highest pressure stage is increased in pressure up to the urea synthesis pressure and recycled to the urea synthesis zone. In the separation zones of the respective decomposition stages, the unreacted ammonium carbamate is thermally decomposed and separated into ammonia and carbon dioxide by indirect heating with steam, etc. The major part of the amount of heat required for the urea production plant is consumed for this heating. There is accordingly a serious problem of how to effectively reduce the amount of heat required for recovering the unreacted materials.

The decomposition reaction of the unreacted ammonium carbamate is highly endothermic. On the other hand, when the mixed gas containing ammonia and carbon dioxide which is obtained as a result of the decomposition of the ammonium carbamate is absorbed in an absorbent, a great amount of heat of absorption is liberated. In order to recover this heat of absorption, it is advantageous to effect the absorptions in the respective stages under conditions of temperature and pressure as high as possible. Where the heat of absorption is recovered in the form of steam, the steam is preferably high in temperature and pressure so that it can be effectively employed for various uses.

Attempts toward recovering the excess of heat in the form of steam of good quality having a urea synthesis temperature and a pressure of 5 kg/cm$^2$ (gauge) or more have heretofore been made and a number of methods have been proposed. In one such method, a recovered ammonium carbamate solution, holding, as sensible heat, the heat of absorption liberated in a high pressure absorption stage, is fed to a urea synthesis zone as it is without recovering the heat in each absorption stage and then the heat of absorption is recovered in a heat exchanger disposed in the urea synthesis zone. In the method described in U.S. Pat. No. 3,944,605, the heat energy liberated in a high pressure absorption zone is transferred to liquid ammonia, the pressure of which is increased to urea pressure, by means of heating the liquid ammonia in a heat exchanger provided in the high pressure absorption zone, and then the excess amount of heat for the urea synthesis is recovered in a heat exchanger disposed in the urea synthesis zone or in a heat recovery zone ahead of the urea synthesis zone, etc. Although these methods are advantageous in obtaining high temperature and high pressure steam, they have the common disadvantage in that the heat exchange is conducted in the urea synthesis zone under high temperature and high pressure conditions and in a highly corrosive fluid, so that the heat exchanger is essentially required to have high resistances to pressure, heat and corrosion, increasing the cost of equipment to a considerable extent.

As described hereinbefore, in the urea concentration step, a small amount of ammonia is discharged together with the condensed water derived from water vapor generated upon the concentration. This previously has not been a serious problem due to its small amount. In recent years, however, intense interest has been shown towards the discharged ammonia due to scaling up of production of the urea production plants. In conventional mediumsized apparatus, it has been almost impossible to economically recover small amounts of ammonia and carbon dioxide from an aqueous urea solution in a finishing step, so that the ammonia and carbon dioxide are discarded together with the waste water. With a large-scale urea production plant, however, the discarded ammonia and carbon dioxide are not negligible in amount. That is, with a large-scale plant, even an extremely small content of ammonia in the waste water reaches a substantial amount since the total amount of waste water becomes very great, causing environmental pollution due to contamination of rivers or seas therewith. There is accordingly a realistic need for the development of an improved process for recovering ammonia by which the loss of valuable ammonia is prevented and the pollution problem is solved. In order to meet this requirement, there has been proposed a process for separating and recovering ammonia and carbon dioxide from an aqueous solution containing traces of ammonia and carbon dioxide by subjecting the aqueous solution to rectification or a stripping treatment using water vapor to separate therefrom a mixed gas composed of ammonia, carbon dioxide and water vapor, and recovering by absorption the mixed gas along with an off-gas obtained by low pressure decomposition of unreacted ammonium carbamate. However, this process has disadvantages in that the heat energy of the steam consumed in the rectification or the stripping treatment is lost during cooling and absorption operations for the mixed gas and that additional cooling water is necessary to remove the heat of condensation of the water vapor. In addition, the steam content of the mixed gas is relatively great, so that the absorbate obtained by absorbing the mixed gas is diluted to a considerable extent. Introduction of such diluted solution into the urea synthesis zone results in reduction in conversion in the urea synthesis reaction. In order to overcome these disadvantages, there has been provided in U.S. patent application Ser. No. 651,569 filed Jan. 22, 1976, a process which comprises subjecting an aqueous solution containing traces of ammonia and carbon dioxide to rectification, and feeding the resulting mixed gas composed of ammonia and carbon dioxide and water vapor to a low pressure decomposition zone for unreacted ammonia carbamate to recover ammonia and carbon dioxide together with the heat required for the rectification. The present invention contemplates providing a process for recovering these unreacted materials and heat in a more efficient manner.

In urea synthesis, it is a common practice to indirectly heat the low pressure decomposition zone for separating unreacted ammonium carbamate by means of a steam heater provided in said decomposition zone. For said heating by indirect heat exchange, the steam must necessarily have a pressure above 5 kg/cm$^2$, it being almost impossible to use steam of a lower pressure. Japanese Patent Publication No. 15015/1970 describes a process for thermally decomposing and stripping off unreacted ammonium carbamate by directly blowing low pressure steam into the unreacted ammonium carbamate containing urea synthesis effluent in a low pressure decomposition zone. However, if the aqueous dilute solution containing ammonia and carbon dioxide which has been produced upon concentration of an aqueous urea solution is discarded as it is similar to conventional practice, the unreacted ammonium carbamate which has not been separated and recovered in the low pressure decomposition zone is lost. On the other hand, in order to separate substantially all of the ammonia and carbon dioxide by steam stripping in the low pressure decomposition zone, the resulting ammonia- and carbon dioxide-free urea synthesis effluent is inescapably brought into contact with hot water vapor in the vacinity of the bottom of the decomposition zone or tower, whereupon hydrolysis of urea undesirably takes place. This is one of the reasons why the process has not been put into commercial practice even though it has the prominent advantage that low pressure steam can be used.

SUMMARY OF THE INVENTION

It is therefore an object of the present invention to provide a process for efficiently and economically recovering unreacted ammonia and carbon dioxide contained in the waste water discharged from the urea concentration step of a urea synthesis.

It is another object of the present invention to provide a process for removing ammonia from the waste water discharged from such urea concentration step, thereby solving the problem of environmental pollution which would otherwise be involved.

It is still another object of the present invention to provide a process for efficiently recovering the heat quality required for separating and recovering unreacted materials from a urea synthesis effluent.

It is a further object of the present invention to provide a process for economically recovering such heat without use of expensive equipment.

Still further objects will become apparent from the following detailed description taken in conjunction with the drawing, and the following specific examples which, while indicating preferred embodiments of the invention, are given by way of illustration only.

In order to attain the above objects, the present inventors have made an intensive study of processes for recovering unreacted materials and heat in urea synthesis and have found that ammonia in the waste water can be recovered by steam stripping together with the heat used for the recovery.

If the steam obtained by heat recovery is not required to be high in pressure according to its proposed use, e.g., when the recovered steam is to be applied to a step of steam stripping of a dilute aqueous ammonia solution produced in the step of concentrating an aqueous urea solution or to a step of low pressure decomposition of unreacted ammonium carbamate contained in a urea synthesis effluent, it is advantageous from the viewpoint of apparatus efficiency that the heat of absorption of unreacted ammonia and carbon dioxide is recovered in the respective absorption stages to produce steam with different pressures.

It has been found that the ammonia and carbon dioxide in the waste water from the step of concentration of an aqueous urea solution can be substantially completely separated from the waste water by a stripping treatment using low pressure steam. This is very advantageous since no heater is employed. Further, it has also been found that in order to decompose ammonium carbamate in a urea synthesis effluent under low pressure conditions, direct heating by injecting steam into the effluent is preferable to indirect heating by heat exchange since lower pressure steam can be utilized and no heater is needed. In addition, if the stripping is stopped at the stage where a small amount of ammonia remains in the solution, i.e., without completely separating ammonia by means of steam stripping alone, the degree of hydrolysis of the urea contained in the solution will be negligible.

The present invention contemplates providing a process for effectively recovering unreacted materials and heat in urea synthesis by appropriately combining the above facts and skillfully constructing the high pressure and low pressure systems in a urea synthesis process.

According to the present invention, there is provided in a proces for recovering unreacted materials and heat in a urea synthesis which comprises: reacting carbon dioxide with ammonia under urea synthesis conditions to produce a urea synthesis effluent containing urea, unreacted ammonium carbamate, an excess of ammonia and water; treating said urea synthesis effluent in a plurality of pressure decomposition stages wherein the pressure is stepwise reduced thereby to decompose said ammonium carbamate into ammonia and carbon dioxide in each stage; separating a mixed gas of ammonia and carbon dioxide from said urea synthesis effluent at each decomposition stage; contacting in turn the mixed gas separated in each decomposition stage with an absorbent under substantially the same pressure as the decomposition pressure in said stage to absorb said mixed gas in said absorbent in stages; recycling the final resulting absorbate containing ammonium carbamate to the urea synthesis zone; concentrating the aqueous urea solution discharged from the final decomposition stage and still containing a small amount of ammonium carbamate thereby to obtain a concentrated aqueous urea solution; condensing water vapor generated upon said concentration to obtain a condensate containing small amounts of ammonia and carbon dioxide; and stripping said condensate to separate and recover said ammonia therefrom, the improvement which comprises absorbing the off-gas from a high pressure decomposition stage in an absorbate which is obtained by absorbing in an absorbent the off-gas from at least one medium pressure decomposition stage, recovering the heat of absorption liberated upon said absorption by an indirect heat exchange in the form of steam having a pressure of 2–4 kg/cm², contacting said steam with said condensate containing small amounts of ammonia and carbon dioxide in a stripping zone to strip off substantially all of the ammonia and carbon dioxide from said condensate, and introducing the discharged steam containing said ammonia and carbon dioxide into a rectification zone of a low pressure decomposition stage to directly heat the urea synthesis effluent, thereby recovering said mixed gas separated from said urea synthesis effluent in the final (or lowest pressure) decomposition stage together with the ammonia and carbon dioxide contained in said steam.

BRIEF DESCRIPTION OF THE DRAWING

The sole FIGURE is a flow-sheet diagram illustrating a method for embodying the present invention.

DESCRIPTION OF THE PREFERRED EMBODIMENTS

In practice of the present invention, the unreacted ammonium carbamate which is contained in the urea synthesis effluent from the urea synthesis zone is decomposed, as is well known in the art, in decomposition stages including at least one high pressure decomposition stage operated under a pressure of from 15 kg/cm² (gauge) to the urea synthesis pressure and a low pressure decomposition stage using a pressure of 1–4 kg/cm² (gauge). In the process of the present invention the high pressure decomposition of the unreacted ammonium carbamate may be effected by stripping with carbon dioxide or ammonia gas under a pressure substantially equal to the urea synthesis pressure, or by a high pressure rectification under a pressure of 15–25 kg/cm² (gauge). Alternatively, the high pressure decomposition may be conducted by the combination of a stage of decomposing the unreacted ammonium carbamate only by reducing to a pressure of 40–100 kg/cm² (gauge) and of a subsequent medium pressure rectification stage under a pressure of 15–25 kg/cm² (gauge).

The ammonia stripper is preferably operated under substantially the same pressure as that of the low pressure decomposition zone, i.e., 2–4 kg/cm² (gauge). Accordingly, the steam to be injected into the ammonia stripper preferably has a pressure substantially equal to the operating pressure of the ammonia stripper. The pressure of the steam to be fed into the ammonia stripper will thus suffice to be as low as 2–4 kg/cm² (gauge). This makes it possible to effectively use recovered steam from the high pressure absorption zone. The steam is used in an amount necessary and sufficient to keep hot a low pressure distillation column when the steam is admitted thereinto through the ammonia stripper, and the amount is generally in the range of 0.05–0.15 kg/kg of produced urea.

In the ammonia stripper, substantially all of the ammonia and carbon dioxide are separated from the waste water. Part of the fed steam is consumed in heating the ammonia stripper and is condensed and discharged from the ammonia stripper together with the waste water. At the same time, substantially all of the steam in the form of a gas mixed with the separated ammonia and carbon dioxide is fed into the low pressure decomposition stage to heat the urea synthesis effluent.

When the urea synthesis effluent containing unreacted ammonium carbamate is subjected to a stripping treatment with steam, the ammonia carbamate is decomposed into ammonia and carbon dioxide. Of these, carbon dioxide is easy to separate. However, in order to completely separate ammonia from the urea synthesis solution, a high temperature is required, resulting in a material increase in hydrolysis of urea by means of hot water vapor. When the steam stripping is stopped at a stage whereby a small amount of ammonia is left in the urea synthesis effluent, the hydrolysis of urea takes place only in negligible degree.

In practicing the invention, it is preferred to feed steam to the mid-section of the distillation column of the low pressure decomposition stage so as to conduct the steam stripping in the upper half of the distillation column and to heat the urea synthesis effluent at 125°–145° C. under a pressure of 1.5–3.5 kg/cm² (gauge). At the same time, the urea synthesis effluent containing a small amount of remaining ammonia is stripped in the lower half of the distillation column with carbon dioxide fed into the bottom of the column thereby to separate most of the remaining ammonia from the urea synthesis effluent. The amount of carbon dioxide to be fed into the column bottom is generally in the range of 0.01–0.2 kg mol/kg mol of produced urea. The carbon dioxide used for the stripping is exhausted from the top of the low pressure distillation column in the form of a mixed gas of ammonia, carbon dioxide and water vapor and is absorbed in an absorbent in the low pressure absorption zone. As a result, since the ammonia/carbon dioxide ratio in the absorption zone is lowered, it is sufficient to use a reduced amount of aqueous absorbent for absorption thereof. This is advantageous in reducing the amount of water recycled to the urea synthesis zone.

Instead of feeding carbon dioxide into the low pressure decomposition zone as described above, the aqueous urea solution which contains a small amount of unreacted ammonium carbamate may be withdrawn from the low pressure distillation column and substantially all of the unreacted ammonium carbamate may be removed therefrom by flashing under substantially normal pressure.

According to the process of the invention, substantially all of the steam used for stripping the aqueous dilute ammonia solution, which steam then contains ammonia and carbon dioxide separated from said aqueous solution, is directly blown into the distillation column of the low pressure decomposition stage for use as a heat source for the column. Substantially all of the steam blown into the low pressure distillation column is condensed in the column and discharged from the bottom thereof as an aqueous urea solution. In a subsequent concentration step, the additional water is evaporated, so that there is no possibility that the amount of water circulating through the entire urea synthesis system is undesirably increased.

The low pressure steam blown into the ammonia stripper is obtained by heat recovery from the high pressure absorption zone, so that the heat exchanger of the high pressure absorption zone need not be provided for preheating liquid ammonia and is easier to construct, with a reduced cost of construction when compared with that required in the process disclosed in U.S. Pat. No. 3,944,605. When compared with known processes such as of the above patent and the like in which the heat of absorption in the high pressure absorption zone is transferred to the urea synthesis zone as sensible heat either of an ammonium carbamate-containing absorbate being fed to the urea synthesis zone or of liquid ammonia, and heat is recovered collectively in the form of high pressure steam by indirect heat exchange in the urea synthesis zone operated under high temperature and high pressure conditions, the process of the present invention is advantageous in that the amount of steam recovered in the urea synthesis zone is reduced, which in turn reduces the required heat transfer area or the size of heat exchanger, and that the cost of construction of the heat exchanger is also reduced since the heat exchanger need not be made of an expensive material as would otherwise be required in known processes using high pressure and high temperature conditions. In cases where new areas are opened for the utilization of steam of a low pressure of 2–4 kg/cm$^2$ (gauge) as in the process of the present invention, it will be uneconomical or rather wasteful to produce high pressure steam of about 5 kg/cm$^2$ (gauge) by the use of an expensive heat exchanger and to use part of the high pressure steam by purposely decreasing the high pressure down to the above-mentioned low pressure.

The process of the present invention wherein steam is produced corresponding to a required pressure, greatly contributes to reduction in cost of equipment. The cost of equipment is further reduced in the invention since the low pressure distillation column is directly heated with the recovered steam, thus requiring no heat exchanger therefor.

The present invention will be understood even more clearly from the following detailed description taken in connection with the accompanying illustrative and non-limiting drawing.

In the drawing, urea is synthesized in urea synthesis column 1 operated under urea synthesis conditions, i.e., at a temperature of about 180°–210° C. and under a pressure of about 200–260 kg/cm$^2$ (gauge). The resulting urea synthesis effluent composed of urea, ammonia, ammonium carbamate, water and biuret is passed through line 2 to reducing valve 3 wherein its pressure is reduced to 30–120 kg/cm$^2$ (gauge), and is further fed through line 4 into high pressure separator 5 wherein unreacted ammonia and carbon dioxide are separated by flashing. Alternatively, and instead of said flashing, the unreacted materials may be separated by distillation with heating in apparatus not shown. The off-gas discharged from high pressure separator 5 and containing ammonia, carbon dioxide and water vapor is sent through line 58 to high pressure absorber 57 operated at substantially the same pressure as that of high pressure separator 5. The urea synthesis effluent discharged from the bottom of high pressure separator 5 is introduced through line 6, reducing valve 7 and line 8, with its pressure being reduced to 10–25 kg/cm$^2$ (gauge), into medium pressure distillation column 9 provided with heater 10 at the bottom thereof, through which high pressure steam of 10 kg/cm$^2$ (gauge) is passed via line 10' for heating the urea synthesis effluent to separate most of the unreacted ammonium carbamate as an off-gas composed of ammonia, carbon dioxide and water vapor. This off-gas is fed through line 48 into medium pressure absorption column 46. The urea synthesis effluent leaving the bottom of medium pressure distillation column 9 and still containing up to 10% of unreacted ammonium carbamate is fed through line 11, reducing valve 12 in which its pressure is reduced to 1.5–3.5 kg/cm$^2$, and also through line 13 into the top of low pressure distillation column 14 which is preferably operated under a pressure of from 1.5 to 3.5 kg/cm$^2$ (gauge) and at a temperature of from 100° to 145° C. Column 14 is directly heated by steam having a pressure of 2–4 kg/cm$^2$ which is fed from ammonia stripper 34, as will be described in detail hereinafter, through line 37 to the mid-section of low pressure distillation column 14 and which contains ammonia and carbon dioxide recovered from the ammonia stripper. Into the bottom of column 14 is blown a portion of make-up carbon dioxide through line 71 in an amount of 0.01–0.2 kg mol/kg mol of produced urea. In low pressure distillation column 14 the unreacted ammonium carbamate is decomposed into ammonia and carbon dioxide by stripping with carbon dioxide in packed column 14' in the lower half portion of column 14 and also by stripping with a mixed gas of steam and carbon dioxide in the upper half portion thereof. Most of the ammonia and carbon dioxide are separated from the top of column 14. The low pressure distillation column 14 is held at a temperature of 100°–120° C. in the top thereof and of 120°–145° C. in the steam-blowing portion. The aqueous urea solution from the bottom of column 14 still contains extremely small amounts of ammonia and carbon dioxide and is fed through line 15, reducing valve 16 and line 17 to vacuum concentrator 18 for concentration. The water vapor generated upon said concentration is introduced through line 22 into surface condenser 23 wherein all of the steam is condensed by indirect heat exchange with a coolant such as cooling water fed through line 24 and discharged through line 25. Vacuum concentrator 18 and surface condenser 23 are connected through lines 22 and 26 with steam ejector 27 driven by high pressure steam from a source not shown through line 28 and discharged through line 28'.

The water vapor evaporated in vacuum concentrator 18 contains a mist or droplets of the aqueous urea solution. Prior to introduction of said water vapor from line 22 into surface condenser 23, the water vapor may be passed into a suitable mist separator such as cyclone separator (not shown) to separate a mist of the aqueous urea solution therefrom. The condensate obtained in surface condenser 23 contains 2 wt. % or less of ammonia and 1 wt. % or less of carbon dioxide and is fed through line 29 to pump 30 to increase its pressure to 1.5–3.5 kg/cm$^2$ (gauge) and is further fed through line 31, heat exchanger 32 and line 33 to ammonia stripper 34. Into the bottom of ammonia stripper 34 is blown through line 60 at a rate of 0.05–0.15 kg/kg of produced urea, low pressure steam at a pressure of 2–4 kg/cm$^2$ (gauge) which is recovered in high pressure absorber 57, so that substantially all of the ammonia and carbon dioxide are separated from the condensate and recovered from the top of stripper 34 in the form of a mixed gas of steam, ammonia and carbon dioxide. This mixed gas is blown into the mid-section of low pressure distillation column 14 through line 37 for recovering ammonia and carbon dioxide from the urea synthesis effluent and at the same time for use as a heat source for said column 14. Ammonia stripper 34 is kept at a temperature of 120°–155° C. and at a pressure of 2–4 kg/cm$^2$ (gauge). The waste water which is discharged from the bottom of ammonia stripper 34 through line 35, heat exchanger 32 and line 36 has residual ammonia and carbon dioxide contents of only 10–20 ppm and 20–50 ppm, respectively, and may be released as it is without involving any environmental pollution.

The aqueous urea solution concentrated in vacuum concentrator is introduced into crystallizer 19 for crystallizing urea to form a urea slurry. The crystalline urea in the slurry is separated from the mother liquor by means of centrifugal separator 20 and fed to a subsequent finishing step through line 21. Meanwhile, the mother liquor separated in centrifugal separator 20 and composed of an aqueous urea solution is fed through line 40 to pump 41, in which its pressure is increased, and further fed through line 42 to low pressure absorber 39 wherein the solution absorbs substantially all of the mixed gas fed from the top of low pressure distillation column 14 through line 38 and composed of ammonia, carbon dioxide and water vapor. The resulting absorbate is passed through line 43 to pump 44 to increase its pressure, and is further fed through line 45 to the top of medium pressure absorption column 46 for use as an absorbent therein. Most of the off-gas from medium pressure distillation column 9 containing ammonia and carbon dioxide is absorbed in medium pressure absorption column 46. In addition, a portion of the urea slurry from vacuum concentrator 18 is circulated by a line not shown through heat exchanger 47 provided in the bottom portion of medium pressure absorption column 46 to recover the heat of absorption generated therein for use as a heat source for concentration of the aqueous urea solution in vacuum concentrator 18.

Unabsorbed ammonia discharged from the top of medium pressure absorption column 46 is passed through line 49 to ammonia condenser 50 to cool and liquefy the ammonia. The liquid ammonia passes through line 51 and is mixed with fresh ammonia from line 72 and then fed to pump 52 to increase its pressure and is circulated through line 53 to heat recovery zone or means 64. The absorbate discharged from the bottom of medium pressure absorption column 46 is fed through line 54 to pump 55 in which its pressure is increased, and further fed through line 56 to high pressure absorber 57 in which the off-gas from high pressure separator 5 composed of ammonia, carbon dioxide and water vapor is admitted through line 58 and absorbed in the absorbent therein. The heat of absorption generated upon the absorption in high pressure absorber 57 is recovered therefrom in the form of steam having a gauge pressure of 2-4 kg/cm$^2$ by means of indirect heat exchange with water introduced from line 73, and by said indirect heat exchange the temperature of the absorption zone of absorber 57 is cooled to allow substantially all of the off-gas from high pressure separator 5 to be absorbed in the solution. High pressure absorber 57 is kept at a temperature of 120°-170° C., preferably of 130°-160° C. and at a pressure of 30-120 kg/cm$^2$ (gauge). High pressure absorber 57 contains a small packed column 57' from which is exhausted ammonia together with any inert gases. The exhausted gas is reduced in pressure in reducing valve 59 and fed through line 59' to medium pressure absorption column 46.

The steam recovered in high pressure absorber 57 is blown through line 60 into ammonia stripper 34. The absorbate from high pressure absorber 57 containing urea, ammonia and carbon dioxide is increased in pressure by feeding through line 61 to pump 62 and is fed through line 63 to heat recovery zone 64. Meanwhile, fresh make-up carbon dioxide from line 67 is compressed in carbon dioxide compressor 68 and fed through line 69 to heat recovery zone 64, and is mixed with both fresh make-up ammonia and recovered ammonia from line 53. In heat recovery zone 64 the absorbate from high pressure absorber 57 together with the make-up carbon dioxide and ammonia forms an aqueous ammonium carbamate solution. This mixture or solution is fed through line 65 to urea synthesis column 1. Heat recovery zone 64 is operated under substantially the same temperature and pressure conditions as those of urea synthesis column 1. The surplus or excess quantity of heat of reaction during formation of the ammonium carbamate in heat recovery zone 64 is recovered from line 66 as steam with a gauge pressure above about 5 kg/cm$^2$ by indirect heat exchange with water introduced from line 74.

If steam of 2-4 kg/cm$^2$ (gauge) is conveniently applicable to use other than supplying steam to ammonia stripper 34, part of the make-up carbon dioxide to be fed into heat recovery zone 64 may be introduced through line 70 to high pressure absorber 57 to increase the quantity of heat generated therein, thereby increasing the amount of recovered steam of low pressure. In this case, the heat exchanger of heat recovery zone 64 may be reduced in size or may be omitted in some cases. This results in reduction both in cost of equipment and in cost of power for compression of carbon dioxide.

In one embodiment of the above process, the decomposition of unreacted ammonium carbamate in high pressure separator 5 may be conducted by stripping with a stripping gas. Suitable stripping gases include ammonia, carbon dioxide and inert gases such as nitrogen, and the preferred stripping gases are ammonia and carbon dioxide.

As discussed hereinabove, the absorbate from high pressure absorber 57 containing urea, ammonia and carbon dioxide is increased in pressure and fed to heat recovery zone 64 wherein it is mixed with make-up carbon dioxide and ammonia to form an aqueous ammonium carbamate solution which is then fed to urea synthesis column 1. It will be understood that the amounts of make-up carbon dioxide and ammonia fed into heat recovery zone 64 will vary depending upon the amounts thereof in the absorbate from high pressure absorber 57 and will be sufficient and in the proportions necessary to form the desired aqueous ammonium carbamate solution. As also discussed hereinabove, portions of the make-up carbon dioxide may be introduced into other areas of the system such as into low pressure distillation column 14.

The present invention will be particularly illustrated by way of the following example.

EXAMPLE

The urea synthesis effluent from urea synthesis column 1 operated under conditions of 195° C. and 230 kg/cm$^2$ (gauge) was composed, all in kg/hr, of 1154 of urea, 1166 of ammonia, 328 of carbon dioxide, 528 of water and 3.5 of biuret. The urea synthesis effluent was flashed through line 2, reducing valve 3 and line 4 into high pressure separator 5 operated at a pressure of 95 kg/cm$^2$ (gauge). In separator 5, an off-gas composed, all in kg/hr, of 263 of ammonia, 42 of carbon dioxide and 13 of water was separated from the urea synthesis effluent. From the bottom of high pressure separator 5 was withdrawn the urea synthesis effluent composed, all in kg/hr, of 1148 of urea, 906 of ammonia, 290 of carbon dioxide, 513 of water and 3.8 of biuret, which effluent was fed through line 6, reducing valve 7 and line 8 to medium pressure distillation column 9 operated at a pressure of 17 kg/cm$^2$ (gauge) wherein most of the ammonia and carbon dioxide were separated by distillation from the urea synthesis effluent. The urea synthesis effluent was then passed through line 11, reducing valve 12 and line 13 to the top of the low pressure distillation column 14 operated at a pressure of 2.3 kg/cm² (gauge), in which most of the residual ammonia and carbon dioxide were separated from the urea synthesis effluent by distillation. Medium pressure distillation column 9 was indirectly heated by means of heater 10 mounted at the bottom thereof and using high pressure steam of 10 kg/cm² (gauge) introduced through line 10'. Low pressure distillation column 14 was heated, without use of any heater, by directly blowing into the mid-section thereof through line 37 steam recovered from ammonia stripper 34 and containing ammonia and carbon dioxide, and was also provided with packed column 14' below said mid-section. Carbon dioxide was blown through line 71 into the bottom of low pessure distillation column 14 which had a top temperature of 110° C. and a bottom temperature of 120° C. The urea synthesis effluent, which was distilled with steam in the upper half portion of low pressure distillation column 14 and which was stripped with carbon dioxide in the lower half portion thereof, was withdrawn from the bottom and found to be substantially an aqueous urea solution containing small amounts of residual ammonia and carbon dioxide. The thus treated urea synthesis effluent (or aqueous urea solution) was fed through line 15, reducing valve 16 and line 17 to vacuum concentrator 18 wherein water and small amounts of dissolved ammonia and carbon dioxide were evaporated at a temperature of 60° C. under a pressure of 80 mmHg. The resulting concentrated aqueous urea solution was fed to crystallizer 19 to crystallize urea, followed by separation of crystalline urea from the mother liquor by means of centrifugal separator 20. The thus separated crystalline urea was fed through line 21 to a granulation step (not shown).

The steam evaporated in vacuum concentrator 18 and containing small amounts of ammonia and carbon dioxide was fed through line 22 to surface condenser 23 and cooled by indirect heat exchange with cooling water which was fed from line 24 and discharged through line 25, thereby condensing substantially all of the steam. Vacuum concentrator 18 and surface condenser 23 were connected through lines 22 and 26 with steam ejector 27 driven by high pressure steam from line 28 and discharged through line 28' and were both held under reduced pressure. The condensate which was obtained in surface condenser 23 and which contained 0.57 wt. % of ammonia, 0.2 wt. % of carbon dioxide and 0.09 wt. % of urea was fed through line 29 to pump 30 to increase its pressure. The condensate was heated in heat exchanger 32 with the waste water from the bottom of ammonia stripper 34. Then, the condensate was fed into ammonia stripper 34 operated under a pressure of 2.5 kg/cm² (gauge) and heated by directly injecting steam obtained by heat recovery as will be described hereinafter, without provision of any heater. From the top of ammonia stripper 34 were distilled off as an off-gas substantially all of the ammonia and carbon dioxide recovered in surface condenser 23 together with 53 kg/hr of water vapor. The mixed gas was used as a heat source by introduction through line 37 into the mid-section of low pressure distillation column 14. The waste water discharged from the bottom of ammonia stripper 34 through the line 35 contained only 20 ppm of ammonia, 12 ppm of carbon dioxide and 20 ppm of urea.

The mother liquor separated in centrifugal separator 20 was passed through line 40, pump 41 and line 42 to low pressure absorber 39 operated under a pressure of 2 kg/cm² to absorb therein the mixed gas of ammonia, carbon dioxide and steam sent from the top of low pressure distillation column 14 through line 38. The resulting absorbate was increased in pressure and fed to medium pressure absorption column 46 operated under a pressure of 16.5 kg/cm² (gauge). The mixed off-gas of ammonia, carbon dioxide and steam from the top of medium pressure distillation column 9 was blown into the bottom of medium pressure absorption column 46 through line 48 for countercurrent contact with the absorbent to allow all of carbon dioxide and water and part of ammonia to be absorbed therein. Part of the urea slurry from vacuum concentrator 18 was circulated to heat exchanger 47 provided at the bottom of the medium pressure absorption column 46 through a line not shown, for recovering the heat of absorption generated in medium pressure absorption column 46 to use as a heat source for concentration of the aqueous urea solution in vacuum concentrator 18.

The ammonia not absorbed in medium absorption column 46 was fed from the top thereof through line 49 to ammonia condenser 50 for condensation by cooling. The recovered liquid ammonia was passed through a line 51 for mixing with fresh ammonia from line 72, the pressure of which was increased to urea synthesis pressure by means of pump 52, and fed through line 53 to heat recovery zone 64 ahead of urea synthesis column 1 at a rate of 1113 kg/hr. The absorbate discharged from medium pressure absorption column 46 was composed, all in kg/hr, of 114 of urea, 380 of ammonia, 342 of carbon dioxide, 203 of water, and 6 of biuret and reached a temperature of 103° C. The absorbate was fed through line 54, pump 55 and line 56 to high pressure absorber 57 operated at a temperature of 150° C. and under a pressure of 94.5 kg/cm² (gauge). At the same time, the mixed gas from high pressure separator 5 and composed, all in kg/hr, of 263 of ammonia, 42 of carbon dioxide and 13 of water vapor was fed through line 58 to high pressure absorber 57 and substantially completely absorbed in the absorbent therein. From small packed column 57' of high pressure absorber was exhausted 1 kg/hr of ammonia together with inert gases. The exhausted gas was reduced in pressure in reducing valve 59 and fed through line 59' to medium pressure absorption column 46.

In high pressure absorber 57, the heat of absorption liberated upon the absorption of said off-gas from high pressure separator 5 was recovered by an indirect heat exchange with water introduced from line 73 in the form of saturated steam having a gauge pressure of 2.5 kg/cm². The amount of recovered steam was 73 kg/hr. This low pressure steam was fed, as described hereinbefore, through line 60 to ammonia stripper 34 in which 20 kg/hr of the steam was consumed and condensed. 53 kg/hr of the remaining steam was passed through line 37 to the low pressure distillation column 14. The absorbate produced in high pressure absorber 57 was composed, all in kg/hr, of 114 of urea, 642 of ammonia, 384 of carbon dioxide, 216 of water and 6 of biuret and was fed through line 61 to pump 62 in which its pressure was raised to the urea synthesis pressure. The thus pressurized absorbate was fed through line 63 to the heat recovery zone 64 operated at a temperature of 180° C. under a pressure of 230 kg/cm² (gauge). To heat recovery zone 64 was also fed through line 69 at a rate of 705 kg/hr make-up carbon dioxide which had been compressed by means of carbon dioxide compressor 68. The absorbent in heat recovery zone 64 was heated by the heat of formation of ammonium carbamate. The hot ammonium carbamate solution was fed through line 65 to the urea synthesis column. In order to maintain the outlet temperature of the urea synthesis column at 195° C., the surplus quantity of heat in heat recovery zone 64 was recovered in the form of saturated steam having a pressure of 5 kg/cm² (gauge) from line 66. The amount of produced steam reached 67 kg/hr. The steam was used as a heat source for a urea melter requiring 5 kg/cm² (gauge) steam or for other purposes. In total, 140 kg/hr of steam was recovered from high pressure absorber 57 and heat recovery zone 64.

What is claimed is:

1. In a process for recovering unreacted materials and heat from a urea synthesis which includes the steps of: reacting carbon dioxide with ammonia under urea synthesis conditions to produce a urea synthesis effluent containing urea, unreacted ammonium carbamate, an excess of ammonia and water; treating said urea synthesis effluent in a plurality of pressure decomposition stages wherein the pressure is stepwise reduced thereby to decompose said ammonium carbamate into ammonia and carbon dioxide in each stage; separating a mixed gas of ammonia and carbon dioxide from said urea synthesis effluent at each decomposition stage; contacting in turn the mixed gas separated in each decomposition stage with an absorbent under substantially the same pressure as the decomposition pressure in said stage to absorb said mixed gas in said absorbent in stages; recycling the final resulting absorbate containing ammonium carbamate to the urea synthesis zone; concentrating the aqueous urea solution discharged from the final decomposition stage and still containing a small amount of ammonium carbamate thereby to obtain a concentrated aqueous urea solution; condensing water vapor generated upon said concentration to obtain a condensate containing small amounts of ammonia and carbon dioxide; and stripping said condensate to separate and recover said ammonia and carbon dioxide therefrom, the improvement which comprises absorbing the off-gas from a high pressure decomposition stage in an absorbate in a high pressure absorption zone, said absorbate being obtained by absorbing in an absorbent the off-gas from at least one medium pressure decomposition stage, recovering the heat of absorption liberated upon said absorption by an indirect heat exchange in the form of steam having a pressure of 2–4 kg/cm² (gauge), contacting said steam with said condensate containing small amounts of ammonia and carbon dioxide in a stripping zone to strip off substantially all of the ammonia and carbon dioxide from said condensate, and introducing the discharged steam containing the ammonia and carbon dioxide into the rectification zone of a low pressure decomposition stage to directly heat the urea synthesis effluent, thereby recovering said mixed gas separated from said urea synthesis effluent in said low pressure decomposition stage together with the ammonia and carbon dioxide contained in said steam.

2. The process as claimed in claim 1 wherein said off-gas from the high pressure decomposition stage is absorbed in said absorbent together with a portion of make-up carbon dioxide.

3. The process as claimed in claim 1 wherein carbon dioxide is introduced into said low pressure decomposition stage.

4. The process as claimed in claim 3 wherein said carbon dioxide is introduced into the bottom portion of the column used for the low pressure decomposition stage, and said discharged steam from said stripping zone is introduced into the mid-section of said rectification zone.

5. The process as claimed in claim 1 wherein said aqueous urea solution discharged from the low pressure decomposition stage is subjected to flashing under substantially normal pressure to separate still remaining unreacted ammonium carbamate prior to said concentration.

6. The process as claimed in claim 1 wherein prior to condensation of said water vapor generated upon said concentration of aqueous urea solution, the mist of the aqueous urea solution contained in said water vapor is separated and recovered from the water vapor with a portion of the ammonia, carbon dioxide and water vapor therein in the form of a condensate containing urea, ammonia and ammonium carbamate.

7. The process as claimed in claim 1 wherein said absorbate obtained by absorbing the off-gas from the high pressure decomposition stage together with make-up carbon dioxide and ammonia is fed to a heat recovery zone to form an aqueous ammonium carbamate solution, the excess amount of heat of reaction is recovered therein in the form of steam by indirect heat exchange with water, and the resultant aqueous ammonium carbamate solution is fed to the urea synthesis zone.

8. The process as claimed in claim 1 wherein said decomposition of unreacted ammonium carbamate in said high pressure decomposition stage is conducted by stripping with a stripping gas.

9. The process as claimed in claim 8 wherein said stripping gas is ammonia.

10. The process as claimed in claim 8 wherein said stripping gas is carbon dioxide.

11. The process as claimed in claim 1 wherein said stripping zone is operated under a pressure of from 2 to 4 kg/cm² (gauge).

12. The process as claimed in claim 1 wherein said low pressure decomposition stage is operated under a pressure of from 1.5 to 3.5 kg/cm² (gauge) and at a temperature of from 100° to 145° C.

13. The process as claimed in claim 1 wherein said high pressure absorption zone is operated at a temperature of from 120° to 170° C. and under a gauge pressure of from 30 to 120 kg/cm².

14. The process as claimed in claim 1 wherein said stripping zone is operated at a temperature of from 120° to 155° C. and under a gauge pressure of from 2 to 4 kg/cm².

* * * * *